United States Patent [19]

Bradstreet

[11] Patent Number: 4,688,557

[45] Date of Patent: Aug. 25, 1987

[54] THERAPEUTIC TRACTION CHAIR

[75] Inventor: Hal R. Bradstreet, North Adams, Mich.

[73] Assignee: Bradstreet Manufacturing Services, Inc., North Adams, Mich.

[21] Appl. No.: 797,648

[22] Filed: Nov. 13, 1985

[51] Int. Cl.$^4$ .................... A61F 5/00

[52] U.S. Cl. .................... 128/71; 128/75; 297/330

[58] Field of Search .................... 128/75, 33, 71, 70, 128/69; 297/316, 330, 340, 411

[56] References Cited

U.S. PATENT DOCUMENTS

| | | | |
|---|---|---|---|
| 913,127 | 2/1909 | Haas | 128/75 |
| 951,560 | 3/1910 | Eaton | 128/75 |
| 1,356,365 | 10/1920 | Hosmer | 128/75 |
| 1,614,641 | 1/1927 | Anderson | 128/75 |
| 2,786,512 | 3/1957 | Moyer | 128/75 X |
| 3,353,532 | 11/1967 | Ellis | 128/75 |
| 3,716,049 | 2/1973 | Kaplan | 128/75 |
| 3,768,464 | 10/1973 | Greissing | 128/75 |
| 3,859,990 | 1/1975 | Simon | 128/75 X |
| 3,975,051 | 8/1976 | Ballagh | 297/434 |

*Primary Examiner*—Edgar S. Burr
*Assistant Examiner*—Moshe I. Cohen
*Attorney, Agent, or Firm*—Beaman & Beaman

[57] ABSTRACT

A therapeutic traction chair for extending the middle and lower back including a seat receiving the patient and a backrest. The seat and backrest comprise a subframe pivotally mounted to a supporting frame wherein the angle of the backrest to the vertical may be adjusted. Arm supports extend from the backrest under the armpits of a seated patient, and the seat is vertically adjustable relative to the backrest to drop the seat away from the backrest transferring the patient's weight to the arm supports placing the spine and back under traction and extension. The adjustment of the subframe and seat position is through an electric-powered actuator, and the arm supports may be positioned to an inactive storage condition.

17 Claims, 12 Drawing Figures

THERAPEUTIC TRACTION CHAIR

BACKGROUND OF THE INVENTION

In the treatment of orthopedic disorders of the back and spine it has long been recognized that relief of pain and therapy results from the placing of the back and spine in traction or extension. Such extension treats injury due to compression of the spine vertabrae and disks, and individuals with chronic middle and lower back pain often find relief for extended periods of time by placing the middle and lower back in traction for a relatively short duration.

A wide variety of traction and extension devices exist, and it is known to use the weight of the patient for traction producing purposes, rather than employ artificial "dead" weight through weight, pulley and cord systems. Examples of traction devices utilizing the weight of the patient are shown in U.S. Pat. Nos. 3,353,532 and 3,716,049.

Specially designed traction apparatus is usually found in hospitals and physical therapy centers and are not readily available to patients in their homes and places of business. While relatively long term relief of pain can often be obtained by placing the back in traction for a relatively short period of time, the inconvenience of visiting a medical center for a traction treatment often prevents frequent visits and back pain is endured because of a lack of ready availability of convenient traction means. While "hang" bars may be mounted in doorways from which patients may suspend themselves by their arms, and "home" traction apparatus is known, most available devices either require excessive exertion on the part of the patient or are large and bulky and troublesome to set up and use.

It is known to incorporate therapeutic apparatus into chairs, examples being shown in U.S. Pat. Nos. 2,786,512 and 3,975,051. It is also known to incorporate traction structure for the head, back and spine into chair-type devices as shown in U.S. Pat. Nos. 913,127; 951,560 and 3,768,464. However, known chair devices are unsightly, complicated, expensive and obviously of such special purpose construction as not to readily blend with ordinary house or office furniture, or to be generally usable for nonorthopedic treatment purposes.

It is an object of the invention to provide a therapeutic traction chair for the treatment of back and spine problems wherein the chair is of attractive appearance, usable for general purpose applications, and is relatively economical to manufacture.

A further object of the invention is to provide a therapeutic traction chair capable of effectively producing a controlled degree of traction on the middle and lower back regions under comfortable conditions requiring minimal exertion on the part of the patient.

Yet another object of the invention is to provide a therapeutic traction chair having a seat and backrest wherein arm supports mounted on the backrest extend under the arms of the patient at the shoulders, and the seat is lowered relative to the backrest to transfer the patient's weight to the arm supports for traction purposes.

An additional object of the invention is to provide a therapeutic traction chair utilizing arm supports extending from a backrest wherein the arm supports may be pivoted between operative and inoperative positions, and may be vertically adjusted with respect to a seat permitting the chair to be adjusted for the most comfortable positions for a given patient.

A further object of the invention is to provide a therapeutic traction chair employing a subframe mounted upon a supporting frame in an adjustable manner wherein the subframe includes a seat and backrest, and an electric actuator movably adjusts the subframe relative to the support frame, and also functions to position the seat to the backrest to control the extent of traction imposed upon a patient supported by arm supports located under the arms and mounted upon the backrest.

The therapeutic traction chair in accord with the invention includes a support frame which rests upon the floor. A subframe is pivotally mounted upon the support frame and includes a seat and backrest, the pivot axis of the subframe being located at a region rearward of the seat front edge. The subframe includes a backrest support supporting a backrest cushion, and a seat support is pivotally mounted on the subframe adjacent the seat forward edge and includes a seat cushion.

At its upper regions the backrest support mounts a pair of spaced arm supports which extend from the backrest for selectively engaging the chair occupant below the arms at the shoulder extending under the armpits. The arm supports are, preferably, both vertically and horizontally adjustable, adjustment in the vertical direction being made through a head rest mounted upon the backrest support, and, preferably, the arm supports are pivotal between use and nonuse positions wherein the arm supports may be moved to a storage or nonuse position when the chair is being used for standard or nontherapeutic purposes.

An electric linear actuator is interposed between the support frame and the subframe. This actuator may be of the electric motor drive type utilizing a threaded or ball nut apparatus for linearly bi-directionally moving an element depending upon the direction of motor rotation. The actuator is pivotally mounted at one end upon the support frame, and at the other end is pivotally attached to the seat support adjacent its rear region, i.e. the region adjacent the backrest.

A stop located upon the subframe limits the pivotal movement between the subframe and seat structure. For instance, upward movement of the rear region of the seat structure will cause the seat structure to engage the subframe stop and the seat will be in a normal relationship to the backrest, and extension of the actuator pivots the subframe in an upward direction. The weight of the chair occupant is transferred from the subframe to the support frame by the subframe pivot and by the actuator.

In use, the chair occupant is seated on the seat with the rear region of the seat support engaging the backrest. For traction purposes, the arm supports will be extending under the armpits. Retraction of the linear actuator permits the entire subframe to pivot in a backward direction which transfers a greater portion of the occupant's weight to the backrest. At a preadjusted and predetermined pivotal position of the subframe, pivoting of the subframe relative to the support frame ceases and further retraction of the actuator lowers the rear portion of the seat relative to the backrest as the seat structure pivots about its pivot axis located on the subframe.

As the rear portion of the seat "drops away" from the backrest, the primary portion of the chair occupant's weight previously supported by the seat is now supported by the arm supports placing the back and spine under traction due to the occupant's weight. The extent of such traction is determined by the angle of the backrest to the vertical, and the degree of lowering that has occurred in the seat.

The chair occupant will remain in the traction condition as long as desirable, and the traction treatment is terminated by the chair occupant energizing the actuator toward an extended condition which "raises" the rear portion of the seat structure toward the backrest and upon the seat structure engaging the subframe stop further actuator extension pivots the subframe, including the seat and backrest, forward toward a normal upright position.

As the tilting of the backrest permits a predetermined portion of the chair occupant's weight to be transferred to the backrest, the degree and extent of extension of the back and spine can be accurately regulated to provide a comfortable, yet effective treatment. The padded arm supports comfortably engage the occupant's arms, and the attitude of the lowered and associated leg rests also contribute to the occupant's comfort. Accordingly, a therapeutic chair in accord with the inventive concepts is able to effectively relieve pain and discomfort existing in the middle and lower back with neglible inconvenience or discomfort to the user, and yet the apparatus is aesthetically acceptable in a home or office environment and capable of being used in a nontherapeutic manner.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Figure 1:
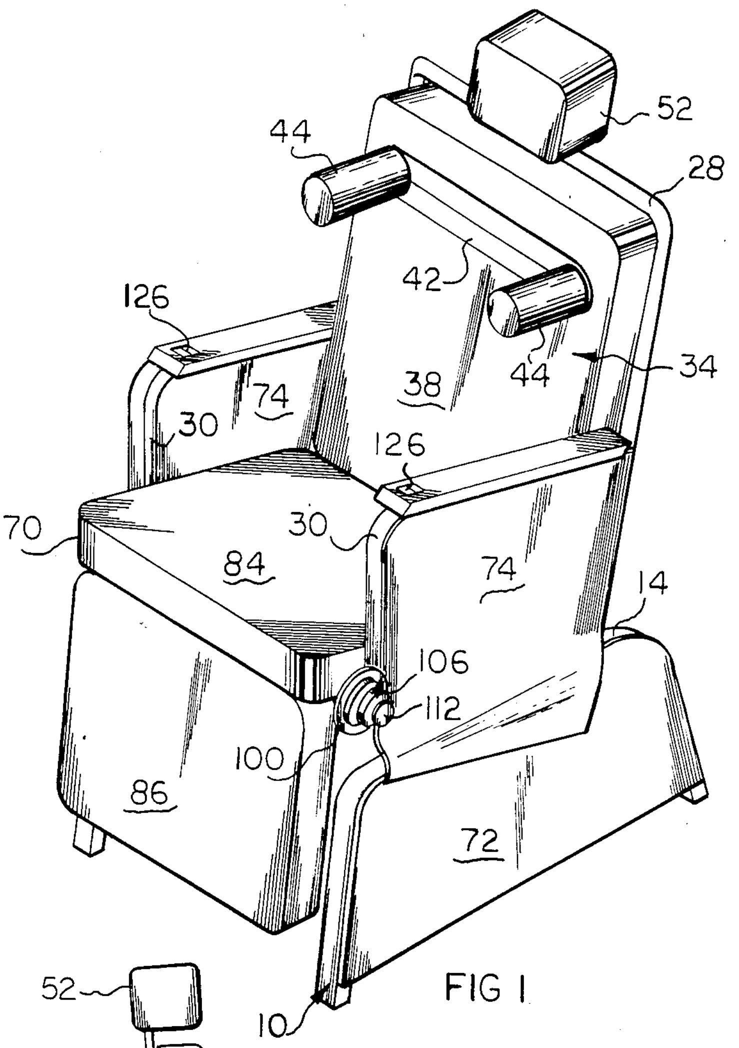
FIG. 1 is a perspective view of a therapeutic traction chair in accord with the invention, the arm supports being extended and the subframe being in the "upright" position.

With reference to FIGS. 1–4, 7 and 8, a therapeutic traction chair in accord with the invention includes a primary support frame 10 formed of tubular elements including legs 12 depending from substantially horizontal portions 14. The support frame 10 consists of four legs 12, two portions 14, bracing elements 16 and connecting braces 18, FIG. 7, which together, define a stable foundation for the chair structure.

A subframe assembly 20 is pivotally mounted upon the support frame 10. The subframe is of a generally L-configuration having vertically extending backrest support elements 22 interconnected by top rail 28 and lower elements 24 extend forwardly of supports 22 and interconnected by the shaft 26. Armrests 30 are affixed to the members 22 and 24.

The subframe 20 is pivotally attached to the support frame 10 by a horizontally disposed pivot shaft 32 supported at its ends within frame portions 14 and extending through the subframe elements 24. In this manner the subframe 20 is capable of pivotal movement with respect to the support frame 10 about a horizontal axis.

A backrest generally indicated at 34 is mounted upon the subframe elements 22. The backrest includes a plywood panel 36, FIG. 7, having a resilient covered cushion 38 affixed thereto. The backrest panel 36 at its upper region is of a width greater than the spacing between supports 22 and engages the front side of the supports while the lower region of the panel is narrower and engages the front side of bar 40 which extends between supports 22, FIG. 8. The cushion 38 includes an elongated opening 42 from which arm supports 44 extend and into which the arm supports 44 may be folded in a storage condition.

Figure 5:
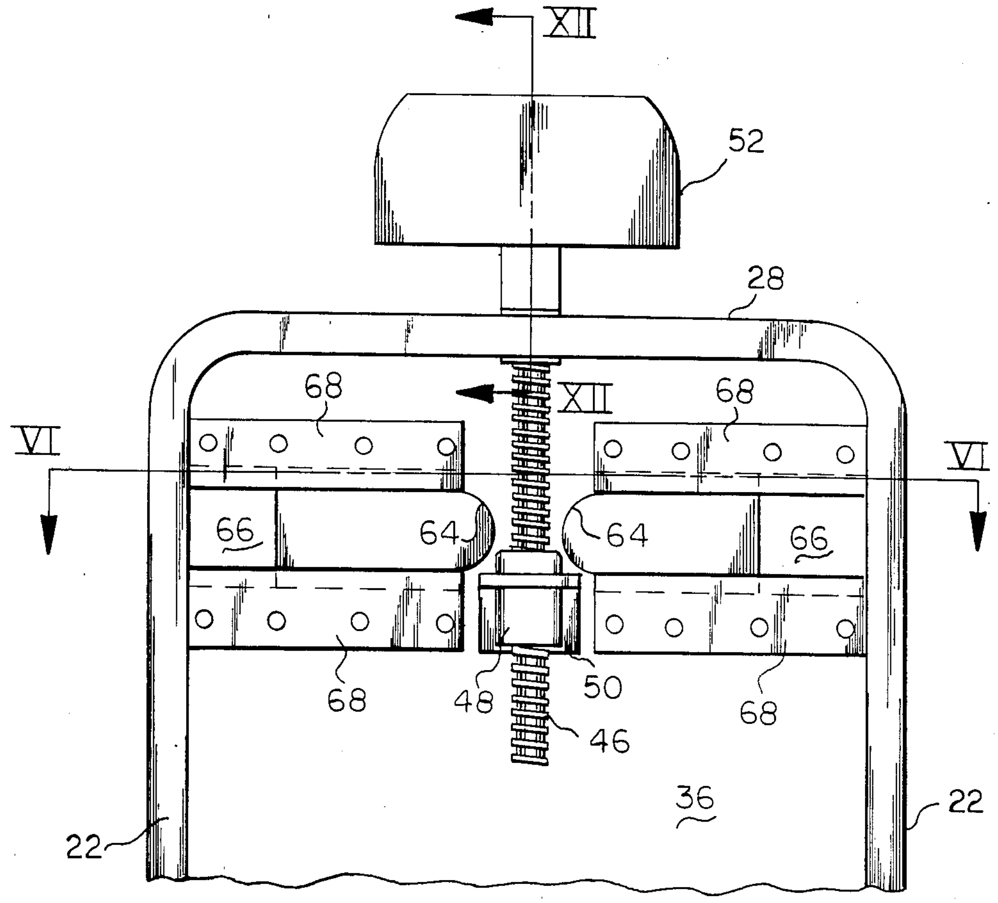
FIG. 5 is a rear, detail view taken of the upper rear portion of the backrest illustrating the adjustable apparatus for the backrest and the arm supports.
Figure 6:
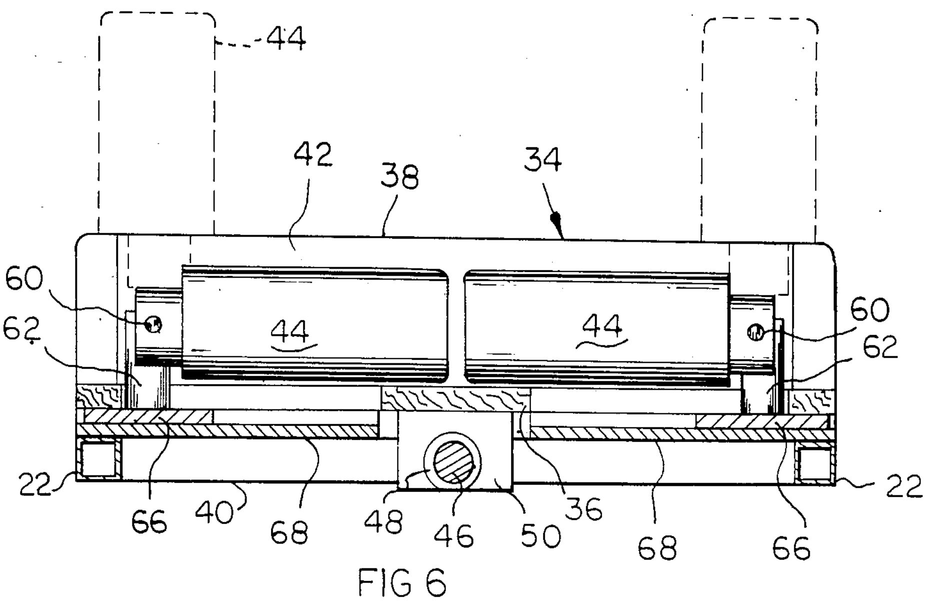
FIG. 6 is a plan, sectional view taken through the backrest above the arm supports along Section VI—VI of FIG. 5.
Figure 7:
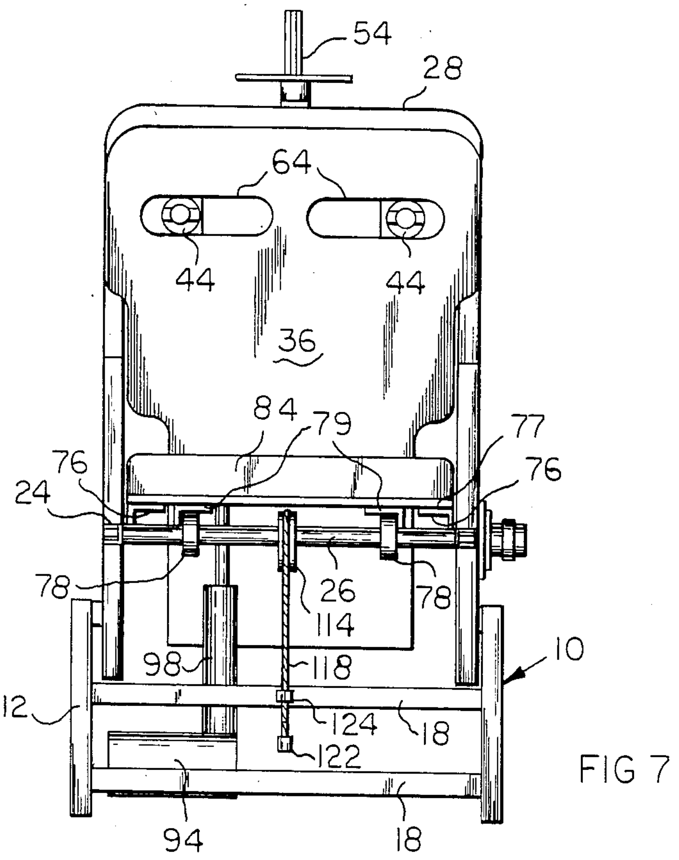
FIG. 7 is a front elevationl view of the chair, the leg support structure and the backrest cushion being removed for purpose of illustration.
Figure 8:
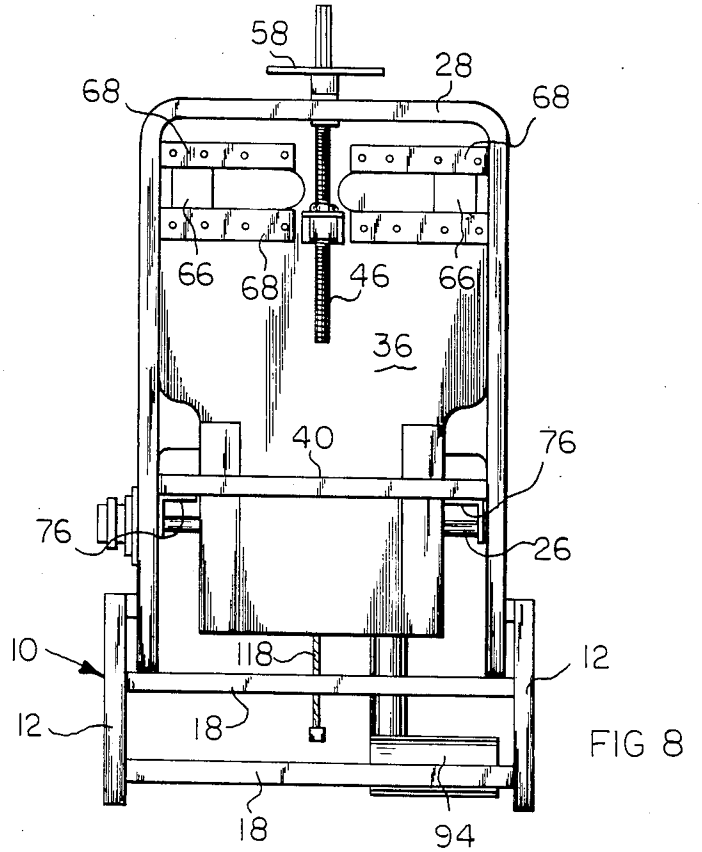
FIG. 8 is a rear elevational view of the chair.
Figure 12:
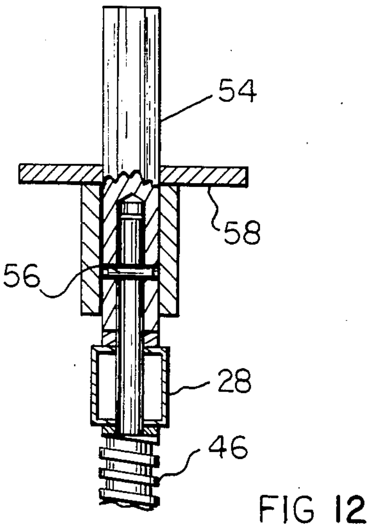
FIG. 12 is an elevational, sectional, detail view of the backrest vertical adjustment structure taken along Section XII—XII of FIG. 5, the headrest cushion not being shown for clarity of illustration.

The backrest 34 is vertically positioned on the subframe 20 by the threaded screw 46 which cooperates with nut 48 attached to the panel 36 by bracket 50, FIGS. 5 and 6. The screw 46 extends through the subframe top rail 28, FIG. 12, and a headrest 52 is attached to the upper end of the threaded shaft by a hexagonal extension 54 pinned at 56 to the screw 46 whereby the rotation of the headrest rotates the screw 46 to vertically adjust the backrest 34 relative to the supports 22. The headrest 52 may be cushioned and provided with foam or other material comfortable to the head and includes a plate 58 having a hexagonal hole receiving extension 54.

The arm supports 44 are each of an elongated configuration pivotally mounted upon the panel 36, FIG. 6, by a pivot pin 60 and a bracket 62. The brackets 62 each extend through a 64 defined in the panel 36 and are each mounted on a slide 66 held against the back of the panel by spaced guides 68 screwed to the panel which overlie the slides. In this manner the arm supports 44 are horizontally adjustable. Each of the arm support is covered with a cushioned material, and is of such length as to be well received under the arms of the chair occupant at the shoulders, i.e. in the armpits, and the arm supports 44 may be pivoted from the storage or inactive position within cushion opening 42 as shown in FIG. 6, to extend from the opening at substantially right angles to the backrest 34 as shown in FIGS. 1–4 to an operative position.

As shown only in FIG. 1, for appearance purposes decorative panels 72 may be mounted on the frame 10, and panels 74 may be attached to the armrests 30 which extend down over the panels 72 to shield the chair under structure from view.

A seat assembly generally indicated at 70 is mounted upon the subframe 20, and the seat assembly includes a pair of spaced angle iron elements 76 located within elements 24 mounted on seat panel 77. Angle iron elements 79 are also attached to panel 77 and are pivotally mounted on shaft 26 by brackets 78 which support the L-shaped panel assembly having the seat panel 77 and leg rest panel 82. The portion 80 serves to support the seat cushion 84, while a leg rest cushion 86 is affixed to the portion 82 depending downwardly from the front edge of the cushion 84. A seat assembly 70 is pivotally mounted upon the subframe 20 on the shaft 26 which functions as a horizontal pivot permitting pivotal adjustment of seat cushion 84 and leg rest cushion 86 relative to the subframe, as later described.

An electrically-powered linear actuator generally indicated at 88 is interposed between the support frame 10 and the rear region of the seat assembly 70 by pivots 90 and 92, respectively. The pivot 92 is a rod extending between elements 76. The linear actuator 88 may consist of a reversible electric motor 94 connected by a right angle speed reduction transmission to a threaded housing and rod assembly including rod 96 wherein the rod may be extended or retracted with respect to the housing 98. The actuator 88 may be of the ball nut type, as well known, and depending on the direction of rotation of the motor 94 the rod 96 will either extend or retract relative to the housing 98 and when the motor is not energized the linear actuator will retain its adjusted length even under compressive forces.

Figure 9:
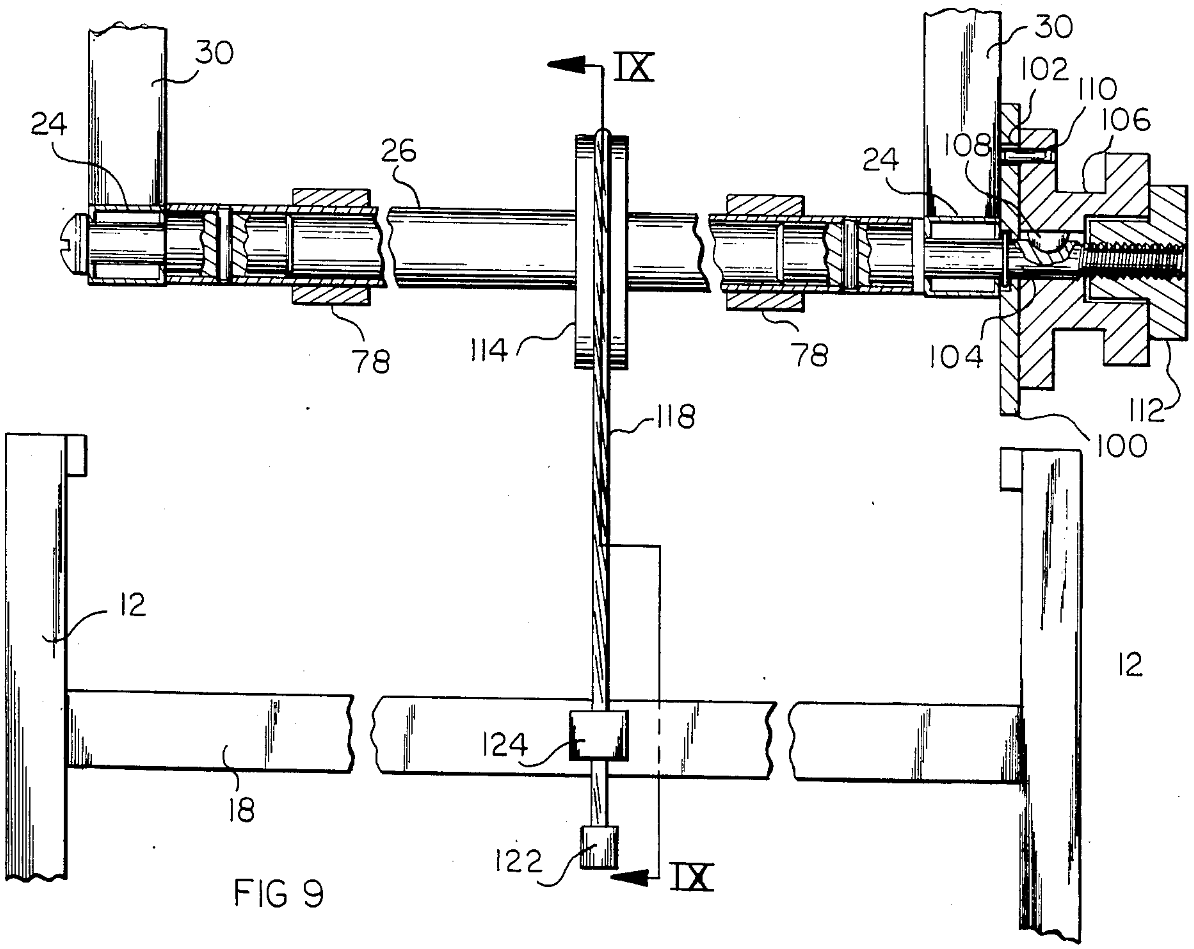
FIG. 9 is a detail, partially sectioned, front elevational view of the subframe tilt angle adjustment structure.

The degree of tilting of the subframe 20 to the frame 10 is controlled by adjustable stop apparatus mounted on the shaft 26. An index plate 100 is fixed to the adjacent element 24 concentric to shaft 26 and includes a plurality of holes 102. The shaft 26 includes an extension 104, FIG. 9, passing through plate 100 having a detent knob 106 keyed thereto by key 108 but axially movable on the shaft extension. The knob 106 includes a detent pin 110 selectively receivable in an index plate hole 102. Tightening of the lock nut 112 forces the knob 106 toward plate 100 and unloosening the nut permits the pin 110 to be placed in a different hole 102. In this manner the rotative position of shaft 26 may be adjusted.

Figure 11:
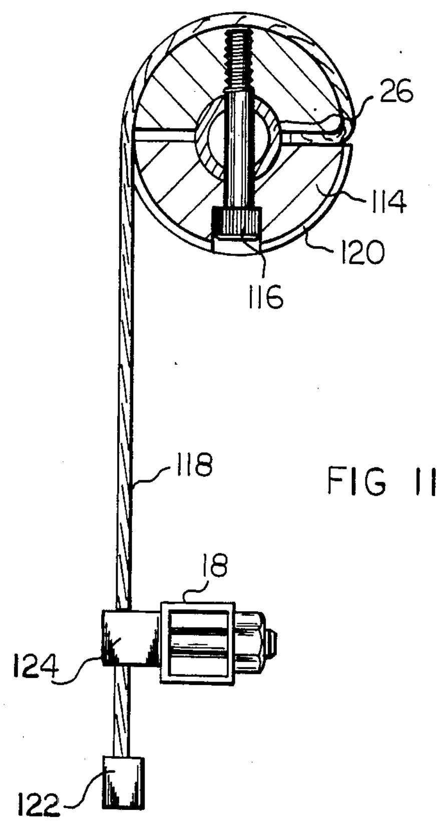
FIG. 11 is an elevational, sectional view of the subframe tilt angle pulley and cable taken along Section XI—XI of FIG. 9.
Figure 10:
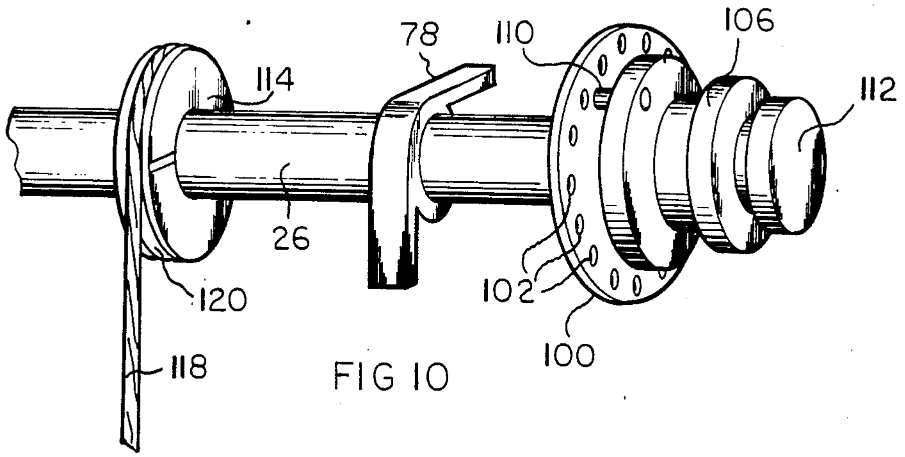
FIG. 10 is a detail perspective view of the subframe tilt angle adjustment structure, per se.

A pulley 114 is fixed on shaft 26 by bolt 116, FIG. 11, and a cable 118 is partially wound in the pulley groove 120. The end of cable 118 has a head 122 affixed thereto and the cable passes through an eye 124 attached to the front brace 18 of support frame 18.

By adjusting knob 106 the distance between head 122 and eye 124 can be varied and as the subframe 20 is tiled on frame 10 in a rearward direction the cable 118 is pulled through eye 124 until the head 122 engages the eye. In this manner the extent of tilt-back of the subframe 20 and backrest 34 can be closely regulated.

Figure 2:
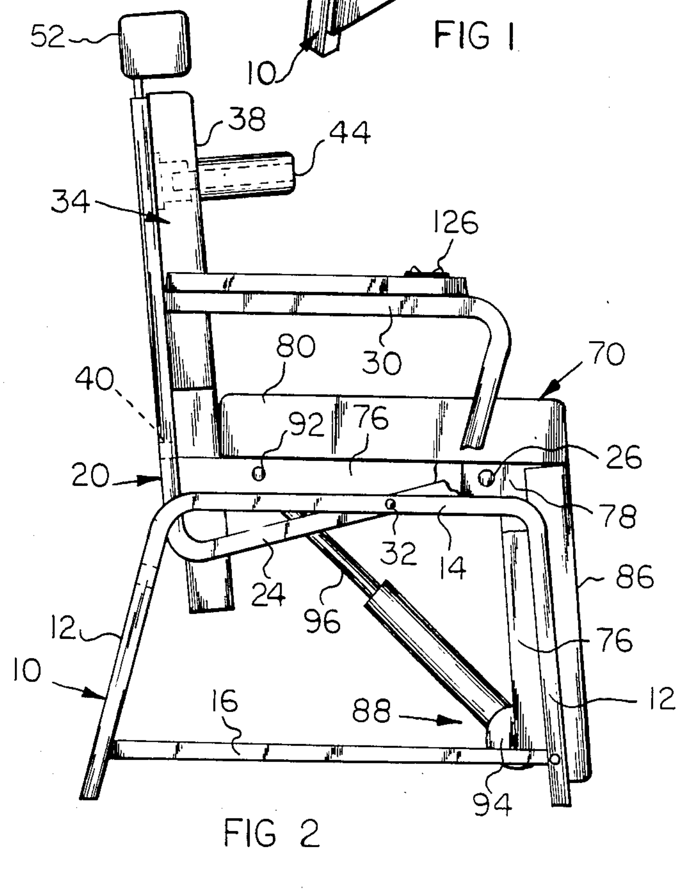
FIG. 2 is a side, elevational view of FIG. 1 as taken from the right side thereof, frame and armrest panels being removed for purpose of illustration.
Figure 3:
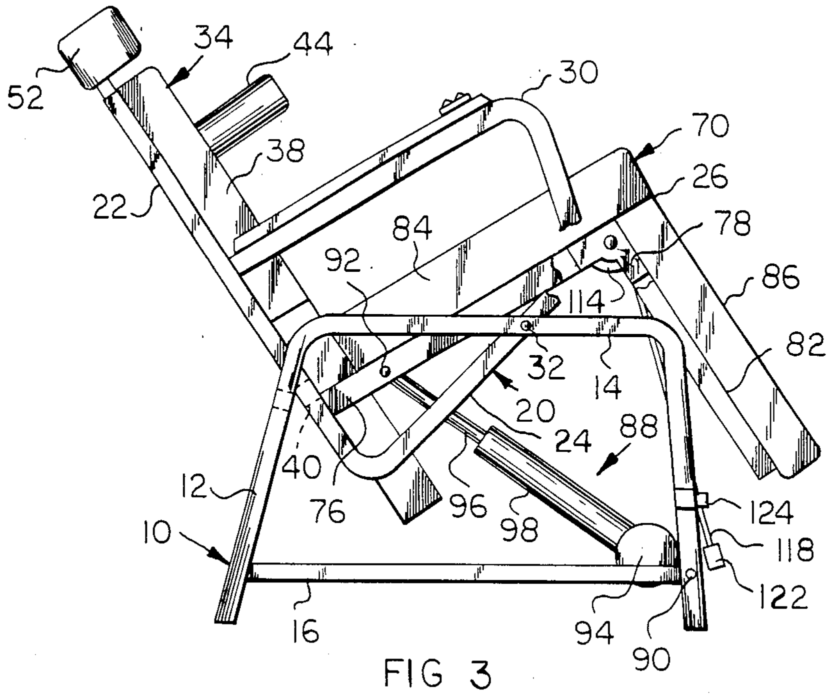
FIG. 3 is a side, elevational view similar to FIG. 2 illustrating the subframe in a tilted condition.
Figure 4:
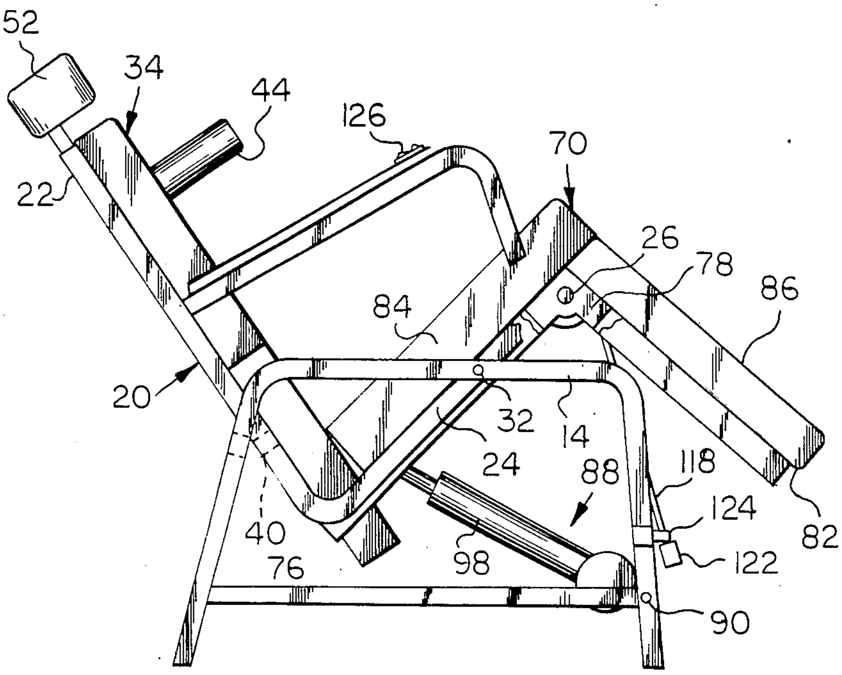
FIG. 4 is a side, elevational view similar to FIG. 3 illustrating the seat structure in a lowered condition.

The normal condition of the components of a therapeutic traction chair in accord with the invention will be as shown in FIGS. 1 and 2 except that the arm supports 44 will be pivoted inwardly to the stored position within backrest opening 42 as shown in FIG. 6. In this condition the motor 94 will have been energized by a control switch 126 mounted on a cushion of armrests 30 to extend the rod 96 its maximum distance which causes maximum clockwise pivoting of the subframe 20 on the frame 10 about pivot 32, as shown in FIG. 2. This pivoting of the subframe 20 occurs due to the engagement of the rear of the seat assembly angle iron elements 76 with the underside of bar 40 and maximum clockwise rotation of the seat assembly 70 about the shaft 26 has also occurred. In this condition the seat cushion 84 will be substantially horizontally disposed, FIG. 2, and the chair may be used in a conventional manner.

When it is desired to use the chair for therapeutic traction purposes the user pivots the arm supports 44 outwardly to the position shown in FIGS. 1–4, and adjusts the vertical height of the backrest 34 on the backrest supports 22 by rotation of the headrest 52. This adjustment is primarily for the purpose of accommodating the various torso lengths of individuals. It is also to be appreciated that the horizontal spacing between the arm supports 44 will need to be adjusted to accommodate various individuals and to this end the arm support brackets 62 may be horizontally adjusted on the backrest panel 36 as slides 66 are moved within guides 68.

Upon the occupant sitting on the seat cushion 84 with the arm supports 44 extending under the armpits, the occupant energizes the motor 94 through a switch 126 to begin retraction of the rod 96 into the housing 98. This retraction of the rod 96 permits the subframe 20 to pivot about pivot shaft 32 in a counterclockwise direction, FIGS. 2–3, transferring a portion of the occupant's weight from the seat cushion 84 to the backrest cushion 38. This pivoting of the subframe 20 continues until the cable head 122 engages the eye 124 and at this time the backward tilting of the subframe ceases. Of course, the position of the cable head 122 has been previously determined by detent knob 106.

Continued retraction of the rod 96 disengages the seat elements 76 from the bar 40 producing a counterclockwise pivoting causing the rear portion of the seat cushion 84 to "drop away" from the lower region of the backrest cushion 38. This lowering of the seat causes the weight of the chair occupant to be supported by the arm supports 44 and a traction condition is imposed upon the occupant's back and spine, particularly the middle and lower back regions, due to the weight of the chair occupant being supported adjacent the shoulders by the arm supports.

The extent of extension can be adjusted by the distance the occupant permits the seat cushion 84 to be lowered. If desired, the seat cushion may be lowered sufficiently to completely remove contact of the cushion with the occupant's buttocks. However, if desired, the lowering of the seat cushion may be terminated to permit a portion of the wearer's weight to be borne by the seat. It will be appreciated that the presence of the leg rest cushion 86 helps support the wearer's legs, and the reclined position of the occupant during traction is comfortable and does not require undue exertion on the part of the patient.

After a traction treatment of the desired duration the occupant will energize switch 126 to reverse the direction of rotation of motor 94 and cause the rod 96 to extend from the housing 98. This action will pivot the seat assembly 70 in a clockwise direction, FIGS. 3 and 4, bringing the seat cushion 84 into full engagement with the occupant for supporting the occupant's weight, and continued clockwise rotation of seat assembly continues until the elements 76 engage the bar 40. Upon such occurrence, continued rod 96 extension pivots the 30. entire subframe 20 in a clockwise direction to pivot the subframe to the normal relationship shown in FIGS. 1 and 2. Thereupon, the arm supports 44 may be pivoted inwardly into their associated opening 42, and the chair utilized in a conventional manner.

By presetting the detent knob 106 which predetermines the angle of the subframe 20 and backrest 34 when the seat cushion 84 begins to lower with respect to the backrest, the percentage of the occupant's weight supported on the arm supports 44 can be regulated and this adjustment in conjunction with the accurate control of the position of the seat cushion 84 permits the amount of extension or tension applied to the patient's back and spine to be accurately regulated to the most comfortable condition.

It will be appreciated that the inventive concepts of the invention can be practiced without utilizing a chair having a tilting subframe. For instance, in a chair with a fixed backrest wherein only the seat is movable for lowering with respect to the backrest, the inventive concepts can be practiced wherein dropping away sufficiently from the backrest to permit that portion of the occupant's weight desired to be supported under the arms by the arm supports. However, the use of the tilting subframe 20 produces the most comfortable arrangement in the practice of the invention, but if the inventive concepts are to be employed in a desk chair, for instance, where sufficient room for tilting of the backrest is not available, the pivoting subframe may not be used.

It is also contemplated that the inventive concepts can be practiced in an embodiment where the seat is fixed and the arm supports, alone, or the backrest and arm supports together are vertically adjustable with respect to the seat. Such an arrangement will still permit a relatively conventionally appearing chair to be used for traction purposes.

It is appreciated that other modifications and variations to the invention may be apparent to those skilled in the art without departing from the spirit and scope of the invention.

I claim:

1. A traction chair comprising, in combination, a frame, a seat defined on said frame, a backrest defined on said frame having a lower region located adjacent said seat and an upper region, a pair of spaced arm supports mounted upon said backrest upper region extending above said seat and positioned to extend under the armpits of an occupant seated upon said seat, and first adjustable means mounting said seat upon said frame said means including actuator means to raise and lower the edge of said seat which is adjacent said backrest whereby the edge of adjacent said backrest said seat may be lowered away from said backrest lower region to transfer the chair occupant's weight to said arm supports to place the spine of the occupant under traction.

2. In a traction chair as in claim 1, adjustable backrest support means mounting said backrest upon said frame permitting tilting of said backrest with respect to the vertical to regulate the extent of traction placed upon the spine of the chair occupant.

3. In a traction chair as in claim 1, second adjustable means mounting said arm supports upon said backrest for adjusting the spacing between said arm supports.

4. In a traction chair as in claim 3, third adjustable means interposed between said backrest and frame for adjusting the vertical position of said arm supports and backrest upon said frame.

5. In a traction chair as in claim 1, pivot means mounting said arm supports upon said backrest whereby said arm supports are pivotal between a storage position adjacent said backrest and an operative position transverse to said backrest.

6. In a traction chair as in claim 5, a cushion defined on said backrest, an opening defined in said cushion, said arm supports extending through said opening, said opening corresponding in configuration to said supports whereby said arm supports are confined within said opening when in said storage position.

7. In a traction chair as in claim 1, backrest mounting means adjustably mounting said backrest upon said frame whereby the angle of said backrest to the vertical may be selectively adjusted to vary the traction force imposed upon the chair occupant.

8. In a traction chair as in claim 7, said backrest mounting means comprising a pivot supporting said backrest upon said frame.

9. In a traction chair as in claim 1, said first adjustable means mounting said seat upon said frame comprising a pivot, said seat including a rear portion adjacent said backrest and a front portion spaced from said rear portion, said seat pivot being located adjacent said seat front portion, and a seat adjuster mounted upon said frame connected to said seat rear portion selectively adjusting the position of said seat rear portion with respect to said backrest.

10. In a traction chair as in claim 9, said seat adjuster comprising a linear actuator, a reversible electric motor drivingly associated with said linear actuator, and a switch controlling said motor.

11. A traction chair comprising, means for producing traction in the spine of an occupant including in combination, a frame, a subframe, a first pivot pivotally mounting said subframe on said frame, a seat defined on said subframe having front and rear portions, a backrest defined on said subframe having lower and upper portions, a second pivot, said seat front portion being pivotally attached to said subframe by said second pivot and said seat rear portion being located adjacent said backrest lower portion, a pair of spaced arm supports mounted upon said backrest upper portion extending above said seat rear portion and positioned to extend under the armpits of an occupant seated upon said seat, and an actuator interposed between said seat rear portion and said frame for adjusting the position of said seat rear portion about said second pivot and relative to said backrest lower portion to adjust the amount of the occupant's weight which is carried by said arm supports and said seat to thereby regulate the traction produced in the spine of the chair occupant.

12. In a traction chair as in claim 11, an adjustable first stop interposed between said frame and said subframe limiting backward pivoting of said subframe, and a second stop defined on said subframe engagable with said seat rear portion limiting upward pivoting of said seat rear portion about said seat front portion pivot whereby said actuator adjusts the pivoting of said subframe upon said frame.

13. In a traction chair as in claim 12, said actuator comprising a linear actuator, a reversible electric motor drivingly connected to said linear actuator and an electric switch controlling said motor.

14. In a traction chair as in claim 11, first adjustable means mounting said arm supports upon said backrest for adjusting the spacing between said arm supports.

15. In a traction chair as in claim 14, second adjustable means interposed between said backrest and frame for adjusting the vertical position of said arm supports and backrest upon said frame.

16. In a traction chair as in claim 11, pivot means mounting said arm supports upon said backrest whereby said arm supports are pivotal between a storage position adjacent said backrest and an operative position transverse to said backrest.

17. In a traction chair as in claim 16, a cushion defined on said backrest, an opening defined in said cushion, said arm supports extending through said opening, said opening corresponding in configuration to said arm supports whereby said arm supports are confined within said opening when in said storage position.

* * * * *

UNITED STATES PATENT OFFICE
CERTIFICATE OF CORRECTION

Patent No. 4,688,557 Dated August 25, 1987

Inventor(s) Hal R. Bradstreet

It is certified that error appears in the above-identified patent and that said Letters Patent are hereby corrected as shown below:

Column 7, claim 1, line 48, cancel "adjacent said backrest"

Column 7, claim 1, line 48, after "seat", insert -- adjacent said backrest --

Signed and Sealed this

Twenty-second Day of December, 1987

*Attest:*

DONALD J. QUIGG

*Attesting Officer*

*Commissioner of Patents and Trademarks*